(12) United States Patent
Onushko et al.

(10) Patent No.: US 11,045,178 B2
(45) Date of Patent: Jun. 29, 2021

(54) CLOSURE DEVICE

(71) Applicant: BOSTON SCIENTIFIC SCIMED, INC., Maple Grove, MN (US)

(72) Inventors: David John Onushko, Minneapolis, MN (US); Lloyd Radman, Blaine, MN (US); Patrick A. Haverkost, Corcoran, MN (US); Jose A. Meregotte, Blaine, MN (US); Joel N. Groff, Delano, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 191 days.

(21) Appl. No.: 16/239,929

(22) Filed: Jan. 4, 2019

(65) Prior Publication Data

US 2019/0200970 A1 Jul. 4, 2019

Related U.S. Application Data

(60) Provisional application No. 62/613,524, filed on Jan. 4, 2018.

(51) Int. Cl.
*A61B 17/00* (2006.01)

(52) U.S. Cl.
CPC ............... *A61B 17/0057* (2013.01); *A61B 2017/00004* (2013.01); *A61B 2017/00575* (2013.01); *A61B 2017/00592* (2013.01); *A61B 2017/00606* (2013.01); *A61B 2017/00676* (2013.01);
(Continued)

(58) Field of Classification Search
CPC ...... A61B 17/0057; A61B 2017/00606; A61B 2017/00575; A61B 2017/00592; A61B 2017/00867; A61B 2017/00004; A61B 2017/00597; A61B 2017/00676; A61B 2017/00654; A61B 2017/00884; A61B 17/12122; A61B 17/12172; A61B 17/12109; A61B 2017/00632; A61B 2017/00243; A61B 17/11;
(Continued)

(56) References Cited

U.S. PATENT DOCUMENTS 5,108,420 A 4/1992 Marks
5,853,422 A * 12/1998 Huebsch ............ A61B 17/0057
606/213

(Continued)

FOREIGN PATENT DOCUMENTS

EP 2399526 A1 12/2011
WO 2016187575 A1 11/2016

OTHER PUBLICATIONS

International Search Report and Written Opinion dated Apr. 3, 2019 for International Application No. PCT/US2019/012311.

*Primary Examiner* — Katherine M Shi
(74) *Attorney, Agent, or Firm* — Seager, Tufte & Wickhem LLP

(57) ABSTRACT

An example closure device is disclosed. The closure device includes a framework including a first end region, a second end region and a medial region extending therebetween. The medical device also includes a biodegradable tissue ingrowth member extending over at least a portion of the framework, wherein the tissue ingrowth member is configured to promote tissue ingrowth thereupon, and wherein the tissue ingrowth is configured to seal an opening in the heart.

20 Claims, 12 Drawing Sheets

(52) U.S. Cl.
CPC ............... *A61B 2017/00867* (2013.01); *A61B 2017/00884* (2013.01)

(58) Field of Classification Search
CPC ..... A61B 2017/1139; A61B 2017/1135; A61F 2002/3009; A61F 2210/0004
See application file for complete search history.

(56) References Cited

U.S. PATENT DOCUMENTS

| | | | |
|---|---|---|---|
| 2002/0010481 A1* | 1/2002 | Jayaraman | A61B 17/0057 606/151 |
| 2003/0139819 A1 | 7/2003 | Beer et al. | |
| 2005/0113868 A1* | 5/2005 | Devellian | A61B 17/12122 606/213 |
| 2005/0251154 A1 | 11/2005 | Chanduszko | |
| 2005/0273119 A1 | 12/2005 | Widomski | |
| 2008/0249562 A1 | 10/2008 | Cahill et al. | |
| 2011/0276075 A1* | 11/2011 | Fung | A61B 18/1815 606/185 |
| 2013/0041404 A1* | 2/2013 | Amin | A61B 17/0057 606/213 |
| 2016/0338706 A1* | 11/2016 | Rowe | A61B 17/0057 |
| 2017/0035434 A1* | 2/2017 | Forbes | A61B 17/12031 |

\* cited by examiner

CLOSURE DEVICE

CROSS-REFERENCE TO RELATED APPLICATIONS

This application claims the benefit of priority under 35 U.S.C. § 119 to U.S. Provisional Application Ser. No. 62/613,524, filed Jan. 4, 2018, the entirety of which is incorporated herein by reference

TECHNICAL FIELD

The present disclosure pertains to medical devices, and methods for manufacturing medical devices. More particularly, the present disclosure pertains to intracorporeal medical devices including a framework connected with other structures, and methods for manufacturing and using such devices.

BACKGROUND

Heart defects including abnormal openings within the heart and vascular system may occur either congenitally or by acquisition. These abnormal openings commonly occur across a septum. A septum is generally defined as a thin wall of tissue that divides two or more cavities (e.g., heart chambers) within the body.

Common congenital heart defect may include ventricular septal defects, atrial septal defects, and patent foramen ovale. Some of these defects may be left-to-right ventricular septal defects which typically result in the left side of the heart having to work harder because some of the blood it pumps will recirculate through the lungs instead of circulating throughout the body. Other defects may include atrial septal defects which typically result in blood being shunted from the left atrium to the right, thus overloading the right side of the heart. These conditions have significant consequences if left untreated. For example, the consequences may include hypertension, increased pulmonary arterial pressure, strain on the heart muscle, and ultimately heart failure.

In some instances, septal defects are corrected by open-heart surgery where a surgeon may cut into the heart and suture the defect closed. However, a variety of methods for treating septal defects that utilize intravascular catheters and closure devices have been developed as less invasive alternatives to open heart surgery. In general, these methods may include a closure device that is delivered to the defect through an intravascular catheter and seals the septal defect.

However, over time, a patient may develop a heart condition in which the treatment option may require advancing a medical device through the septum of the patient. Further, in some instances it may be desirable to cross back through the septal defect (which has been sealed by the closure device). Therefore, it may be desirable to design closure devices which sufficiently seal a septal defect while also permitting a medical device to be passed back through the closure device at a future time point. Closure devices designed to both close a septal defect while permitting medical devices to pass therethrough are disclosed.

BRIEF SUMMARY

This disclosure provides design, material, manufacturing method, and use alternatives for medical devices. An example medical device includes a framework including a first end region, a second end region and a medial region extending therebetween. The medical device also includes a biodegradable tissue ingrowth member extending over at least a portion of the framework, wherein the tissue ingrowth member is configured to promote tissue ingrowth thereupon, and wherein the tissue ingrowth is configured to seal an opening in the heart.

Alternatively or additionally to any of the embodiments above, wherein the tissue ingrowth member is configured to biodegrade after the opening has been sealed.

Alternatively or additionally to any of the embodiments above, wherein the first end region, the second end region, or both the first and second end region include a curved portion extending circumferentially around a longitudinal axis of the framework.

Alternatively or additionally to any of the embodiments above, wherein the curved portion forms a first aperture within the first end region and a second aperture within the second end region and wherein the framework is configured to permit a medical device to pass through the first aperture and the second aperture.

Alternatively or additionally to any of the embodiments above, wherein the framework includes a biodegradable material.

Alternatively or additionally to any of the embodiments above, wherein the framework is designed to biodegrade after the opening has been sealed.

Alternatively or additionally to any of the embodiments above, wherein the tissue ingrowth member includes a fabric covering.

Alternatively or additionally to any of the embodiments above, wherein the tissue ingrowth member includes an electrospun material.

Alternatively or additionally to any of the embodiments above, wherein the framework includes a spiral-shaped member extending along the first end region, the second end region or both the first end region and the second end region.

Alternatively or additionally to any of the embodiments above, wherein the first end region and the second end region of the framework are designed to press against tissue adjacent to the opening in a heart.

Another example occlusion device for sealing an opening in the heart, comprising:

a support scaffold including a first support member, a second support member and a connecting member extending therebetween;

a fabric pouch extending over a least a portion of the support scaffold;

wherein the fabric pouch is configured to promote tissue ingrowth thereupon, and whereby the tissue ingrowth is configured to seal an opening in the heart.

Alternatively or additionally to any of the embodiments above, wherein the scaffold, the fabric pouch or both the scaffold and the pouch include a biodegradable material.

Alternatively or additionally to any of the embodiments above, wherein the first support member, the second support member, or both the first and second support members include a curved portion extending circumferentially around a longitudinal axis of the scaffold.

Alternatively or additionally to any of the embodiments above, wherein the curved portion forms a first aperture within the first support member and a second aperture within the second support member and wherein the scaffold is configured to permit a medical device to pass through the first aperture and the second aperture.

Alternatively or additionally to any of the embodiments above, wherein the fabric pouch includes an electrospun material.

Alternatively or additionally to any of the embodiments above, wherein the scaffold includes a spiral-shaped member extending along the first support member, the second support member or both the first end support member and the second support member.

Alternatively or additionally to any of the embodiments above wherein the first support member and the second support member are designed to press against tissue adjacent to the opening in a heart.

An example method of occluding an opening in the heart, the method comprising:

advancing an occlusion device to a position adjacent the opening, wherein the occlusion device includes:
 a framework including a first end region, a second end region and a medial region extending therebetween; and
 a biodegradable tissue ingrowth member extending over at least a portion of the framework;

deploying the first end region on a first side of the opening;

deploying the second end region on a second side of the opening opposite the first side.

Alternatively or additionally to any of the embodiments above, wherein deploying the first end region on a first side of the opening includes positioning the framework against the tissue defining the first side of the opening.

Alternatively or additionally to any of the embodiments above, wherein deploying the second end region on a second side of the opening includes positioning the framework against the tissue defining the second side of the opening such that the first end region and the second end region of the framework press against tissue adjacent to the opening.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
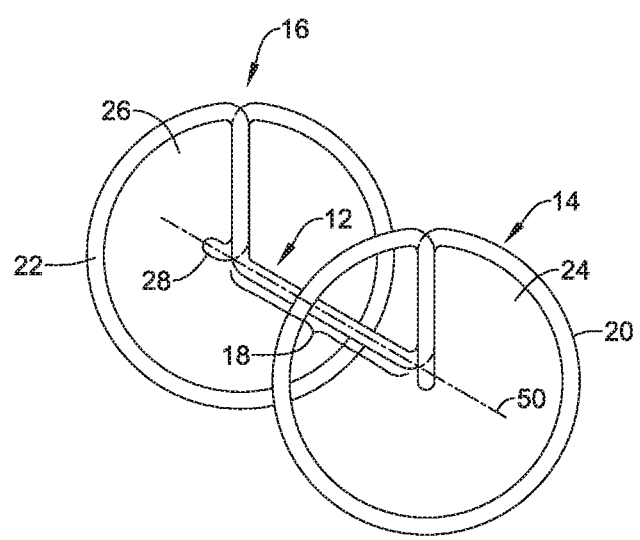
FIG. 1 is a perspective view of an example framework.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

As discussed above, example closure devices which are designed to close openings in the heart are disclosed herein. The example closure devices disclosed herein may be referred to as "occluders" or "occlusion devices." As will be discussed in greater detail below, any of the closure devices disclosed herein may be utilized to close a septal defect including, but not limited to, ventricular septal defects, atrial septal defects, patent foramen ovale, etc. Further, any of the example closure devices disclosed herein may be designed to be deployed across (e.g., on either side of) a septal defect whereby the closure device may pinch and/or press against the tissue walls in which the opening of the septal defect exists. In some examples, a closure device may include a covering disposed along the closure device. The covering may be designed to encourage endothelial tissue to grow thereon, thereby sealing the opening of the septal defect.

Figure 2:
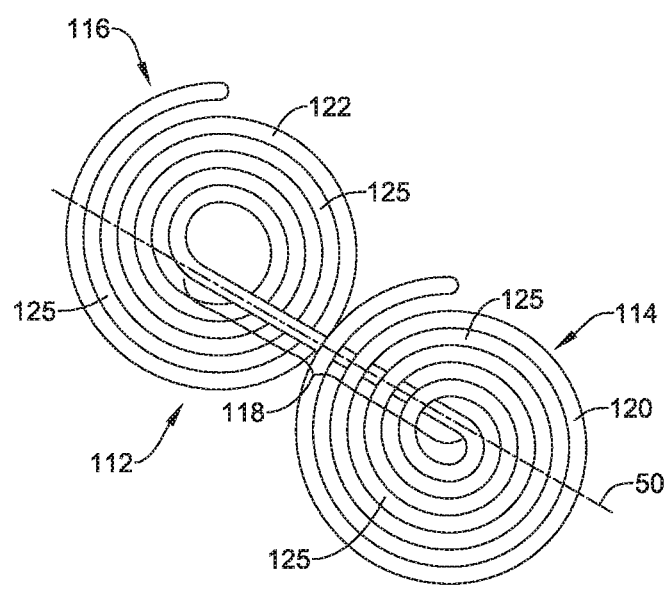
FIG. 2 is a perspective view of another example framework.
Figure 3:
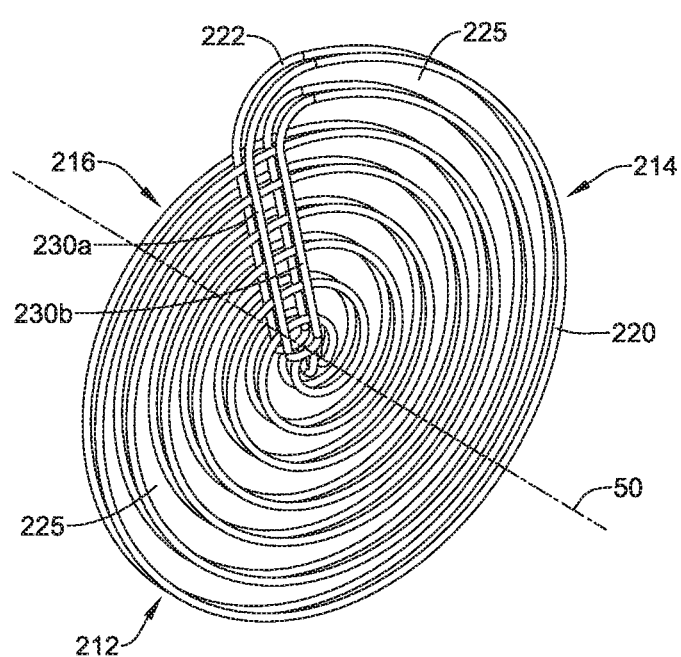
FIG. 3 is a perspective view of another example framework.

FIGS. 1-3 illustrate different example frameworks that may be utilized with a closure device (which will be described in greater detail below). For example, FIG. 1 illustrates an example framework (e.g., support scaffold) 12. The framework 12 may include a first end region 14, a second end region 16 and a medial region 18. The medial region 18 may extend between and connect the first end region 14 with the second end region 16. Additionally, FIG.

1 illustrates that the medial region 18 may space the first end region 14 away from the second end region 16.

The framework 12, or components thereof, may be constructed from a variety of materials. For example, the framework 12, or components thereof, may be constructed from a metal (e.g., Nitinol®). In other instances, the framework 12, or components thereof, may be constructed from a polymeric material (e.g., PET, PLGA, etc.). In yet other instances, the framework 12, or components thereof, may be constructed from a combination of metallic and polymeric materials. Additionally, the framework 12, or components thereof, may include a bioabsorbable and/or biodegradable material. A non-limiting list of example materials which may be utilized to construct the framework 12 or components thereof is listed below.

Additionally, the framework 12 may be constructed of one or more wires (e.g., a metallic wire, a polymeric wire, or combinations thereof) having a substantially circular cross-section. However, this is not intended to be limiting. For example, the wire may have a triangular, ovular, square, or other geometric-shaped cross-section. Additionally, the wire may be solid or tubular. For example, a tubular wire may include a lumen extending therein. Further, the framework 12 may include multiple wires which are braided together to form the framework 12.

In other examples, the framework 12 may be constructed of a polymeric material. For example, the framework 12 may include a solid or tubular polymer material. The polymer material may have a triangular, ovular, square, or other geometric-shaped cross-section. Additionally, in some examples a tubular polymeric material may include a lumen extending therein.

FIG. 1 further illustrates that the first end region 14 and/or the second end region 16 may include a first curved portion 20 and a second curved portion 22. It can be appreciated from FIG. 1 that the first curved portion 20 and the second curved portion 22 may extend around a longitudinal axis 50 of the framework 12. It can be appreciated from FIG. 1 that the first curved portion 20 and the second curved portion 22 form the first end region 14 and the second end region 16, respectively, into substantially circular end regions. It can be further appreciated that the substantially circular shape of the first end region 14 and the second end region 16 may each define a first aperture 24 (defined by the first circular portion 20) and a second aperture 26 (defined by the second circular portion 22). The first aperture 24 and the second aperture 26 may be aligned along the longitudinal axis 50 of the framework 12. As will be discussed in greater detail below, it can be appreciated that the open space defined by the first aperture 24 and/or the second aperture 26 may permit a secondary medical device to pass through the framework 12 when the closure device 10 is positioned within an opening in the heart (e.g., after the closure device 10 has been deployed in a septal defect).

FIG. 1 further illustrates that the framework 12 may include a connection member 28. In general, the connection member 28 may couple with the distal end of a delivery device utilized to advance, manipulate, position and/or deploy the framework 12. It is contemplated that a variety of difference attachment techniques may be utilized to couple the connection member 28 to an example delivery device. For example, the connection member 28 may be a threaded connection, press fit connection, a snare or any other similar connection.

FIG. 2 illustrates another example framework 112. The framework 112 may be similar in form and function to the framework 12 discussed above. For example, the framework 112 may include a first end region 114, a second end region 116 and a medial region 118. The medial region 118 may extend between and connect the first end region 114 with the second end region 116. Additionally, FIG. 2 illustrates that the medial region 118 may space the first end region 114 away from the second end region 116.

The framework 112, or components thereof, may be constructed from a variety of materials. For example, the framework 112, or components thereof, may be constructed from a metal (e.g., Nitinol®). In other instances, the framework 112, or components thereof, may be constructed from a polymeric material (e.g., PET). In yet other instances, the framework 112, or components thereof, may be constructed from a combination of metallic and polymeric materials. Additionally, the framework 112, or components thereof, may include a bioabsorbable and/or biodegradable material. Additionally, while FIG. 2 illustrates that the framework 112, or components thereof (e.g., a wire forming framework 212) may have a substantially circular cross-section, other cross-sectional shapes are contemplated. For example, the framework 112 may include a triangular, ovular, square, or other geometric-shaped cross-section.

FIG. 2 further illustrates that the first end region 114 and/or the second end region 116 may include a first curved portion 120 and a second curved portion 122. It can be appreciated from FIG. 2 that the first curved portion 120 and the second curved portion 122 may extend around a longitudinal axis 50 of the framework 112. It can be appreciated from FIG. 2 that the first curved portion 120 and the second curved portion 122 (which form the first end region 114 and the second end region 116) may be substantially spiral-shaped. It can be further appreciated that each of the spiral-shaped first end region 114 and the spiral-shaped second end region 116 may include one or more openings (e.g., spacing, apertures) 125 between the individual curved portions 120 which define the spiral portion of the first end region 114 and/or the second end region 116.

In some examples, the spiral portion of the first end region 114 and/or the second end region 116 may wind in a clockwise direction. In other examples, the spiral portion of the first end region 114 and/or the second end region 116 may wind in a counter-clockwise direction. Further, in some examples, both the first end region 114 and the second end region 116 may wind in a clockwise direction, both in a counter-clockwise direction, or one of the first end region 114 or the second end region 116 may wind in a clockwise direction while the other winds is a counter-clockwise direction.

Additionally, it can be appreciated that the spiral configuration of the first end region 114 and/or the second end region 116 may increase the overall surface area of the framework 112 which may contact tissue when positioned adjacent an opening (e.g., the opening of a septal defect) in the heart. As will be discussed in greater detail below, it can be appreciated that the openings 125 may permit a secondary medical device to pass through the framework 112 when the framework 112 is positioned within an opening in the heart (e.g., after the framework 112 has been deployed in a septal defect).

FIG. 3 illustrates another example framework 212. The framework 212 may be similar in form and function to other example frameworks discussed above. The framework 212 may include a first end region 214, a second end region 216 and a medial region which may connect the first end region 214 with the second end region 216. Additionally, the medial region may space the first end region 214 away from the second end region 216.

The framework 212 disclosed herein may be constructed from a variety of materials. For example, the framework 212, or components thereof, may be constructed from a metal (e.g., Nitinol®). In other instances, the framework 212, or components thereof, may be constructed from a polymeric material (e.g., PET). In yet other instances, the framework 212, or components thereof, may be constructed from a combination of metallic and polymeric materials. Additionally, the framework 212, or components thereof, may include a bioabsorbable and/or biodegradable material. Additionally, while FIG. 3 illustrates that the framework 212 or components thereof (e.g., a wire forming framework 212) may have a substantially circular cross-section, other cross-sectional shapes are contemplated. For example, the framework 212 or components thereof may include a triangular, ovular, square, or other geometric-shaped cross-section.

FIG. 3 further illustrates that the first end region 214 and/or the second end region 216 may include a first curved portion 220 and a second curved portion 222. It can be appreciated from FIG. 3 that the first curved portion 220 and the second curved portion 222 may extend around a longitudinal axis 50 of the framework 212. It can be further appreciated from FIG. 3 that the first curved portion 220 and the second curved portion 222 (which form the first end region 214 and the second end region 216) may be substantially spiral-shaped. It can be further appreciated that each of the spiral-shaped first end region 214 and the spiral-shaped second end region 216 may include one or more openings (e.g., spacing, apertures) 225 between the individual curved portions 220 which define the spiral portion of the first end region 214 and/or the second end region 216.

FIG. 3 illustrates that the framework 212 may be formed from a single wire member having a first end and a second end that has been attached to one another to form a loop. The wire loop may then be formed into the shape of the framework 212 shown in FIG. 3. Accordingly, it can be appreciated from FIG. 3 that the wire loop may include a first wire portion 230a and a second wire portion 230b. The first wire portion 230a and the second wire portion 230b may be extend (e.g., be positioned) parallel to one another as the wire loop is shaped to form the framework 212 as shown in FIG. 3. For example, the first wire portion 230a and the second wire portion 230b may spiral in parallel to one another to form the spiral end region 214 and/or the spiral end region 216 of the framework 212.

In some examples, the spiral portion of the first end region 214 and/or the second end region 216 may wind in a clockwise direction. In other examples, the spiral portion of the first end region 214 and/or the second end region 216 may wind in a counter-clockwise direction. Further, in some examples, both the first end region 214 and the second end region 216 may wind in a clockwise direction, both in a counter-clockwise direction, or one of the first end region 214 or the second end region 216 may wind in a clockwise direction while the other winds is a counter-clockwise direction.

Additionally, it can be appreciated that the spiral configuration of the first end region 214 and/or the second end region 216 may increase the overall surface area of the framework 212 which may contact tissue when positioned adjacent an opening (e.g., the opening of a septal defect) in the heart. As will be discussed in greater detail below, it can be appreciated that the openings 225 may permit a secondary medical device to pass through the framework 212 when the closure device 210 is positioned within an opening in the heart (e.g., after the closure device 210 has been deployed in a septal defect).

Figure 4:
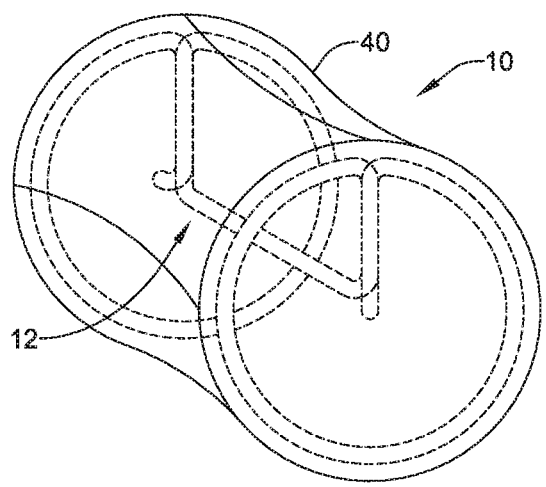
FIG. 4 is a perspective view of an example closure device including a covering.

FIG. 4 illustrates an example closure device 10. The closure device 10 may include the framework 12 described above. However, this is not intended to be limiting. Rather, it is contemplated that the closure device 10 may utilize any of the frameworks described above.

FIG. 4 further illustrates that the closure device 10 may include a covering 40 disposed along the framework 12. The covering 40 may be referred to as a tissue-ingrowth member, pouch, bag, sack, cuff, sleeve, etc. Further, it can be appreciated from FIG. 4 that the covering 40 may substantially surround, encapsulate, cover, etc. the framework 12. However, it is also contemplated that, in some examples, the covering 40 may only cover a portion of the framework 12.

The covering 40 may be formed from a variety of materials. For example, the covering 40, or components thereof, may be formed from a fabric. The fabric may be formed from individual fibers and/or filaments which have been woven, knitted, etc. together to form the covering 40. In other examples, the covering 40, or components thereof, may be constructed from a metal material (e.g., metallic wires and/or filaments). In yet other instances, the covering 40, or components thereof, may be constructed from a polymeric material (e.g., PET, PVDF, ePTFE, etc.). In some examples, the material utilized to construct the covering 40 may be electrospun. Additionally, the covering 40, or components thereof, may be constructed from a combination of fabric, metallic and/or polymeric materials. Further, the covering 40, or components thereof, may include a bioabsorbable and/or biodegradable material.

In some examples, it may be desirable to design the covering 40 such that it encourages the growth of tissue (e.g., endothelial cells) thereupon. For example, the materials utilized to construct the covering 40 may be chosen for their ability to encourage growth of endothelial cells or similar tissue thereon. Additionally, the material utilized to construct the covering 40 may include a particular surface texture (not shown in the figures) which encourages the growth of endothelial cells or similar tissue thereon. In other examples, the covering 40 may include a coating (not shown in the figures) which encourages the growth of endothelial cells or similar tissue thereon.

Figure 5:
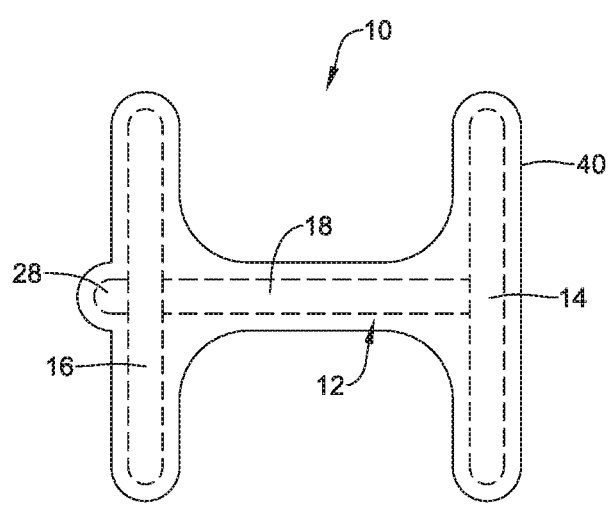
FIG. 5 is a side view of the example closure device illustrated in FIG. 4.

FIG. 5 illustrates a side view of the closure device 10 including the framework 12 and the covering 40. As described above, FIG. 5 illustrates that the covering 40 may surround and/or encapsulate the framework 12 (including the first end region 14, the second end region 16, the medial region 18 and the connection member 28). Further, FIG. 5 illustrates that the covering 40 may substantially follow the shape of the framework 12.

Figure 6:
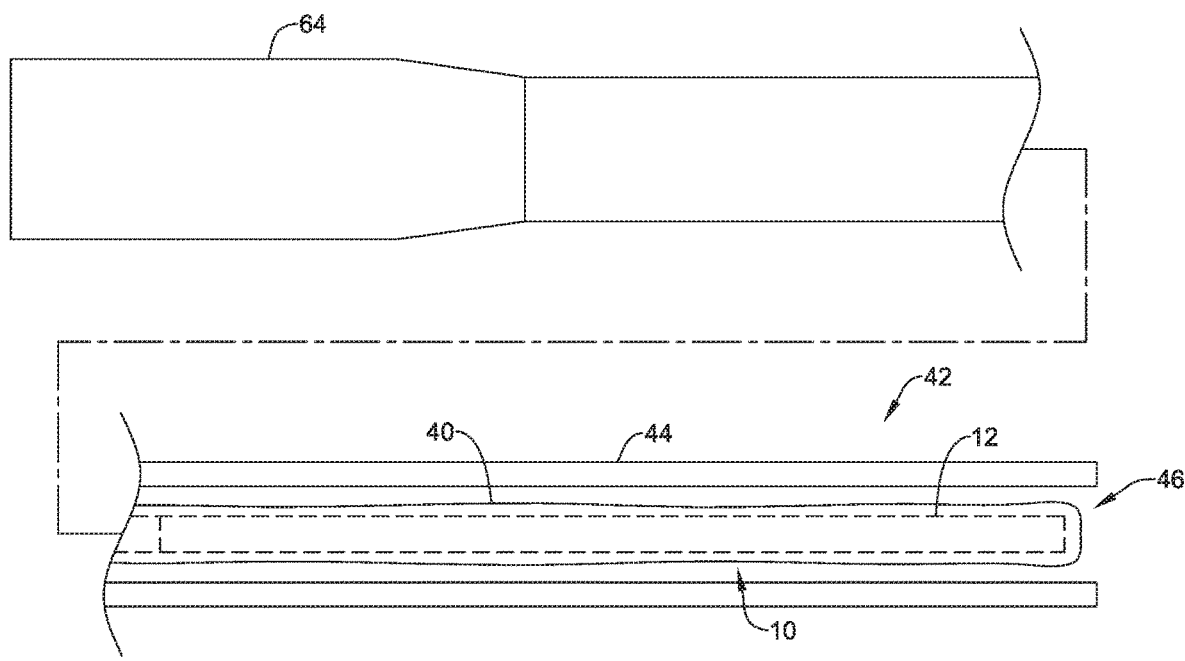
FIG. 6 is an example closure device positioned inside a delivery catheter.

FIG. 6 illustrates a portion of an example medical device delivery system 42. As shown in FIG. 6, the medical device delivery system 42 may include an outer shaft 44 having a lumen 46 extending therein. The outer shaft may be coupled to a handle member 64. FIG. 6 further illustrates that the closure device 10 (including framework 12 and covering 40) maybe positioned within the lumen 46 of the tubular shaft 44. It can be appreciated that FIG. 6 illustrates a configuration in which the closure device 10 is positioned within the delivery system 42 in preparation for deployment at a target site within the body. FIG. 6 further illustrates that the framework 12 may be shaped into a straight configuration for loading into the lumen 46 of the outer shaft 44. Additionally, it can be appreciated that the framework 12 may be constructed form a shape-memory material (e.g., Nitinol®) which allows the framework to return to the shape of the framework 12 illustrated in FIG. 1 after the framework is deployed from the outer shaft (as illustrated and discussed below).

Figure 7:
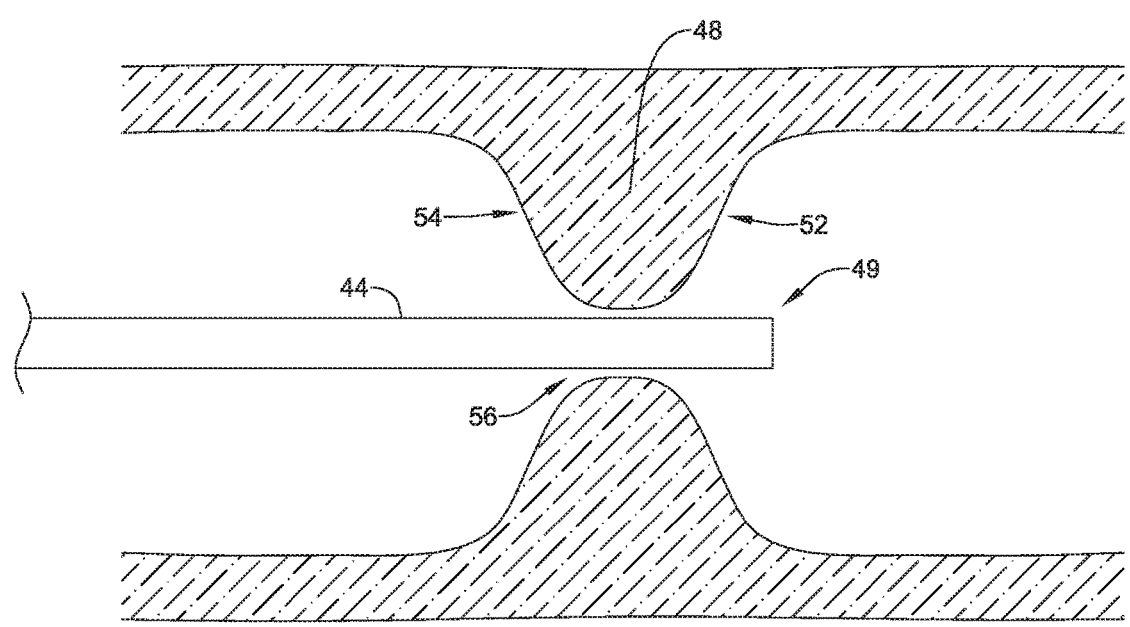
FIGS. 7-9 illustrate an example closure device being deployed across an example opening in the heart.
Figure 8:
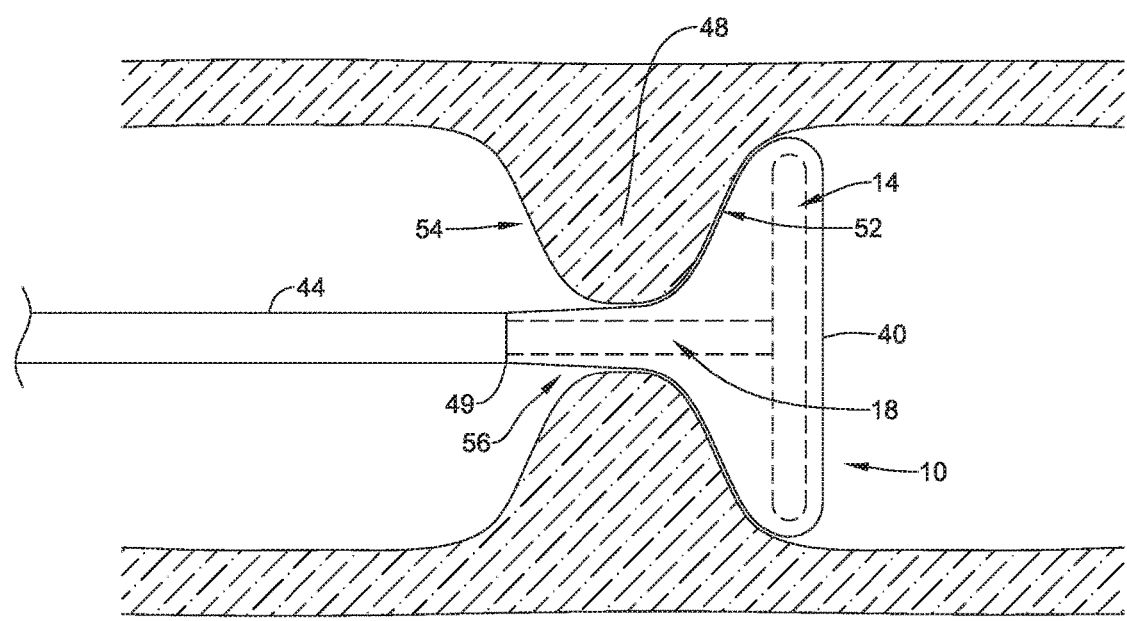
Figure 9:
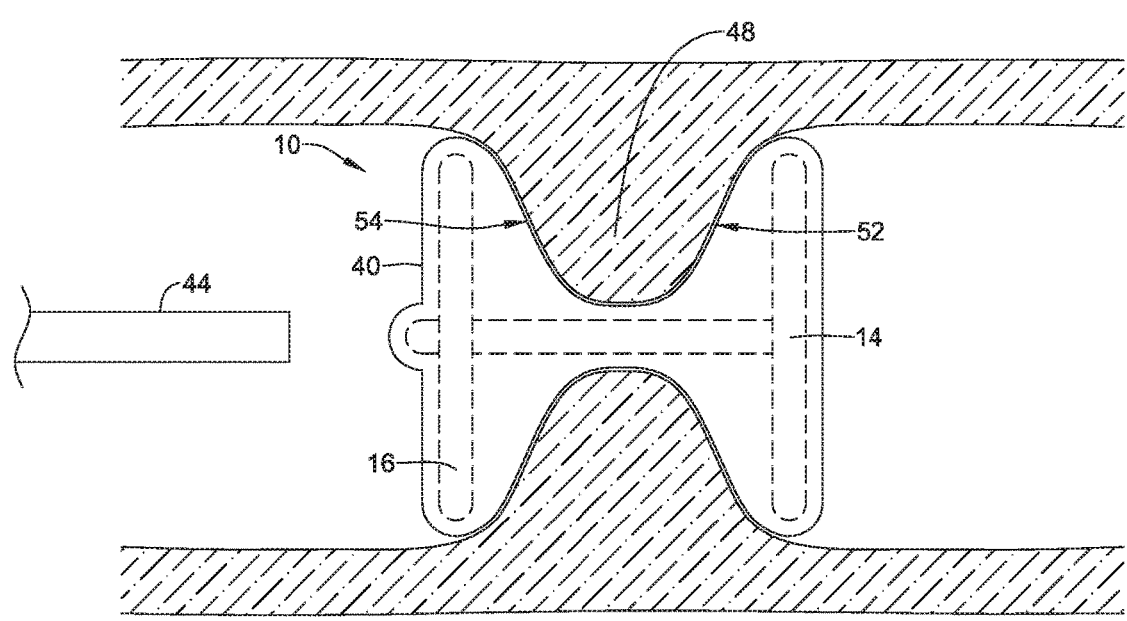

FIGS. 7-9 illustrate the delivery and deployment of the example closure device 10 in an example opening in the heart (e.g., a septal defect in the heart). FIG. 7 illustrates the outer shaft 44 of the example delivery system 42 (discussed above) being advanced to a position adjacent an example septal defect 48. The septal defect 48 includes a first tissue face 52 and a second tissue face 54. The first tissue face 52 and the second tissue face 54 are positioned on opposite ends of an opening 56 which extends through the tissue "wall" of the septal defect. Accordingly, FIG. 7 illustrates that a distal end 49 of the outer shaft 44 has been advanced through the opening 56 (e.g., through the tissue wall of the septal defect 48) to a position in which it extends past the first tissue face 52.

FIG. 8 illustrates an example first step in deploying the closure device 10 including the framework 12 (shown as a dashed line) and the covering 40 (shown as a solid line) from the outer shaft 44. As can be appreciated, the handle member 64 (shown in FIG. 6) may be utilized to retract the outer shaft 44 relative to the closure device 10 In some examples, the outer shaft 44 may be retracted to a position in which the distal end 49 of the outer shaft 44 may be positioned adjacent to the second tissue face 54 of the septal defect 48. It can further be appreciated that retraction of the outer shaft 44 may "uncover" (e.g., deploy) a portion of the closure device 10. For example, retraction of the outer shaft 44 may uncover (e.g., deploy) the first end region 14 of the framework 12 and a portion of the covering 40 surrounding the first end region 14.

It can further be appreciated from FIG. 8 that the first end region 14 of the framework 12 may be manipulated to position the covering 40 such that it presses against the first tissue face 52 of the septal defect 48. In other words, a clinician may pull the framework 12 toward the first tissue face 52 such that it presses against the first tissue face 52. FIG. 8 further illustrates that the medial portion of the framework 12 may span the opening 56 of the septal defect 48.

FIG. 9 illustrates an example second step in deploying the closure device 10 including the framework 12 (shown as a dashed line) and the covering 40 (shown as a solid line) from the outer shaft 44. As can be appreciated, the handle member 64 (shown in FIG. 6) may be utilized to further retract the outer shaft 44 relative to the closure device 10 such that the second end region 16 of the closure device 10 is uncovered and fully deployed from the outer shaft 44.

After being deployed from outer shaft 44, the second end region 16 of the framework may be positioned such that the covering 40 presses against the second tissue face 54 of the septal defect 48. It can be appreciated that the framework 12 may be designed such that its first end region 14 and the second end region 16 may compress, pinch, squeeze, etc. against the first tissue face 52 and the second tissue face 54 of the septal defect 48. In other words, the framework 12 may be designed to shift from a first substantially linear configuration (when loaded in the outer shaft 44) to a deployed configuration in which the framework 12 is shaped similar to the shape shown in FIG. 1. When deployed, the medial region 18 of the framework 12 may be designed to pull the first end region 14 and the second end region 16 toward one another, thereby imparting a compressive force along the first tissue face 52 and the second tissue face 54 of the septal defect 48. Accordingly, it can be appreciated that pressing the framework 12 against the first tissue face 52 and the second tissue face 54 of the septal defect 48 may position the covering 40 adjacent to the tissue surrounding the septal defect.

Figure 10:
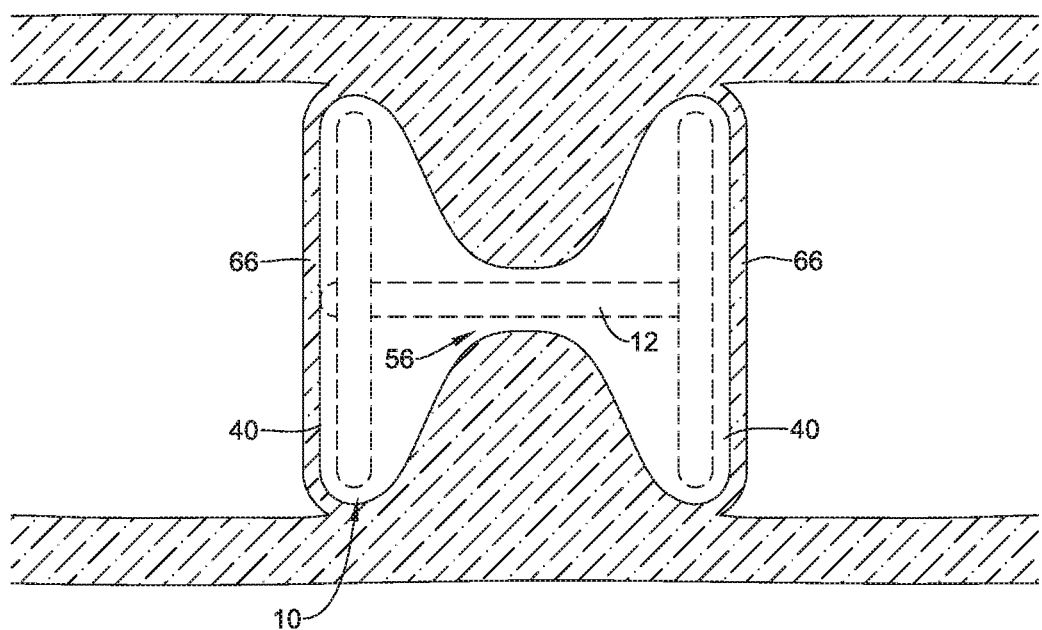
FIG. 10 illustrates tissue growth along the closure device shown in FIG. 9.

FIG. 10 illustrates the closure device 10 including the framework 12 (shown as a dashed line) and the covering 40 (shown as a solid line) positioned adjacent to the septal defect 48 described above. Further, FIG. 10 illustrates that tissue 66 (adjacent to the septal defect 48) has grown along the covering 40 (after a period of time, for example). In some examples, the tissue 66 may completely cover the covering 40 (thereby sealing the septal defect 48) after about 1 to 7 days, or about 7 to 30 days, or about 30 to 90 days, or about 90 to 120 days. As shown in FIG. 10, the tissue 66 has grown along the covering which is adjacent to the first end region 14 and the second end region 16 of the framework 12. It can be appreciated that the tissue growth 66 may seal the opening 56 of the septal defect, thereby preventing fluids (e.g., blood) from passing through the opening 56. However, in other examples, the covering 40 may be designed such that it may limit that amount of tissue 66 that grows thereupon and also permits a particular amount of fluid (e.g., blood) to pass therethrough. In other words, the covering 40 may be porous in some examples.

As discussed above, in some instances it may be desirable for a clinician to access portions of the heart at a time point (e.g., months or years) after the closure device 10 has been implanted in a patient. Further, in some examples it may be desirable for a clinician to access regions of the heart by passing a secondary medical device through the opening 56 described above. In some examples this may be accomplished by passing a secondary medical device through the tissue 66, through the covering 40 and through the first aperture 24 (not shown in FIG. 10, but described above in FIG. 1) and the second aperture 26 (not shown in FIG. 10, but described above in FIG. 1).

It can be further appreciated that in some instances it may be desirable to remove the cover 40 and/or the framework 12 from the septal defect 48, thereby reducing the number of obstacles a clinician may encounter when attempting to advance a secondary medical device through the septal defect. Therefore, in some instances it may be desirable to design the closure device 10 such that the framework 12 and/or the covering biodegrade over time.

Figure 11:
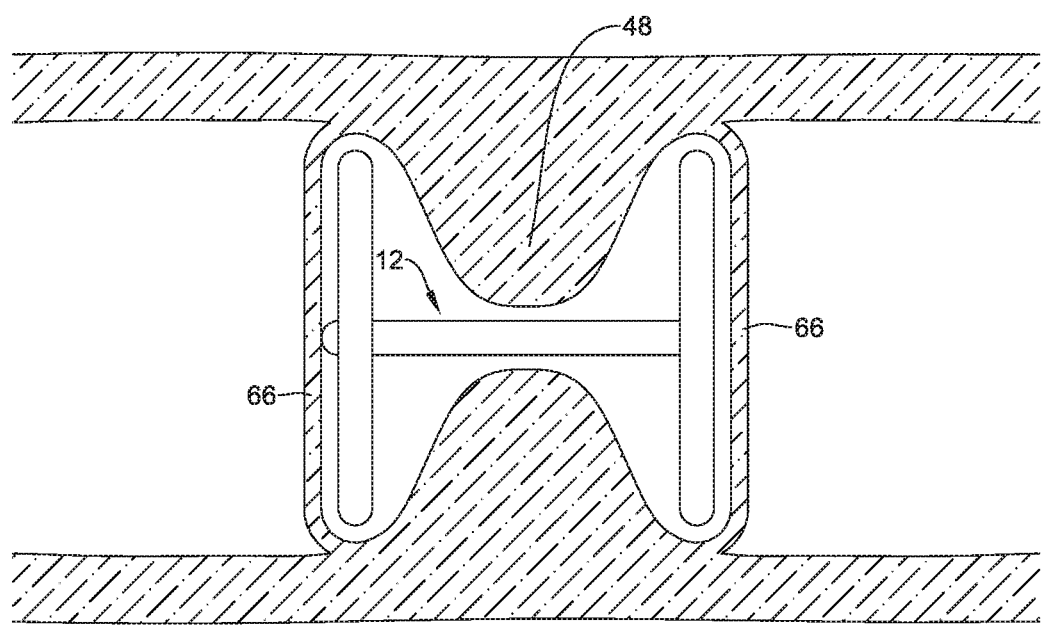
FIGS. 11-12 illustrate the biodegradation of the closure device and covering illustrated in FIG. 10.

FIG. 11 illustrates the framework 12 positioned in the opening after a biodegradable covering 40 has biodegraded. The framework 12 shown in FIG. 11 as a solid line as it is no longer surrounded by the covering 40.

Figure 12:
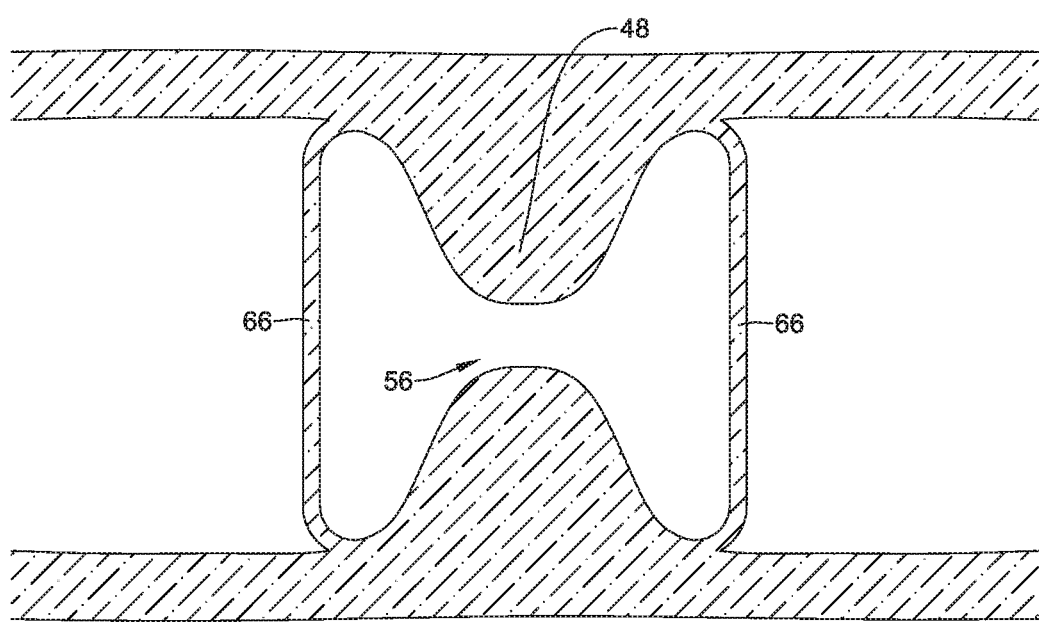

Additionally, FIG. 12 illustrates the septal defect 48, including opening 56, after the biodegradable framework 12 has biodegraded. FIGS. 11-12 illustrate that the tissue 66 may remain adjacent the septal defect 48 after the framework 12, the covering 40 or both the framework 12 and covering have biodegraded.

The materials that can be used for the various components of the closure device 10 and components thereof and the various tubular members disclosed herein may include those commonly associated with medical devices. For simplicity purposes, the following discussion makes reference to the closure device 10 and components thereof. However, this is not intended to limit the devices and methods described herein, as the discussion may be applied to other closure devices and components thereof discussed herein.

The closure device 10 and components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the closure device 10 and components thereof may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the closure device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of closure device 10 or components thereof to achieve the same result.

In some embodiments, a degree of Magnetic Resonance Imaging (MRI) compatibility is imparted into the closure device 10 and components thereof. For example, the closure device 10, or portions thereof, may be made of a material that does not substantially distort the image and create substantial artifacts (e.g., gaps in the image). Certain ferromagnetic materials, for example, may not be suitable because they may create artifacts in an MRI image. The closure device 10, and components thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device, comprising:
   a framework including a first end region, a second end region and a medial region extending therebetween,
   wherein the first end region and second end region each includes a spiral-shaped member comprising a first wire portion and a second wire portion,
   wherein the first wire portion and the second wire portion spiral in parallel to one another and
   a biodegradable tissue ingrowth member extending over at least a portion of the framework,
   wherein the biodegradable tissue ingrowth member is configured to promote tissue ingrowth thereupon, and wherein the tissue ingrowth is configured to seal an opening in a heart.

2. The medical device of claim 1, wherein the biodegradable tissue ingrowth member is configured to biodegrade after the opening has been sealed.

3. The medical device of claim 1, wherein the spiral-shaped members of the first and second end regions extend circumferentially around a longitudinal axis of the framework.

4. The medical device of claim 3, wherein the spiral shaped member of the first end region forms a first aperture within the first end region and the spiral-shaped member of the second end region forms a second aperture within the second end region and wherein the framework is configured to permit a medical device to pass through the first aperture and the second aperture.

5. The medical device of claim 1, wherein the framework includes a biodegradable material.

6. The medical device of claim 5, wherein the framework is designed to biodegrade after the opening has been sealed.

7. The medical device of claim 1, wherein the biodegradable tissue ingrowth member includes a fabric covering.

8. The medical device of claim 1, wherein the biodegradable tissue ingrowth member includes an electrospun material.

9. The medical device of claim 1, wherein the first end region and the second end region of the framework are designed to press against tissue adjacent to the opening in the heart.

10. The medical device of claim 1, wherein the spiral-shaped member of the first end region and the spiral-shaped member of the second end region spiral in a same direction about a longitudinal axis of the medical device.

11. The medical device of claim 1, wherein the spiral-shaped member of the first end region and the spiral-shaped member of the second end region spiral in a different direction about a longitudinal axis of the medical device.

12. The medical device of claim 1, wherein the first wire portion and the second wire portion separated from each other by a gap.

13. An occlusion device for sealing an opening in a heart, comprising:
   a scaffold including a first support member, a second support member and a connecting member extending therebetween,
   wherein the first support member and second support member each includes a spiral-shaped member comprising a first wire portion and a second wire portion, wherein the first wire portion and the second wire portion spiral in parallel to one another and
   a fabric pouch extending over a least a portion of the scaffold,
   wherein the fabric pouch is configured to promote tissue ingrowth thereupon, and whereby the tissue ingrowth is configured to seal an opening in the heart.

14. The occlusion device of claim 13, wherein the scaffold, the fabric pouch or both the scaffold and the fabric pouch include a biodegradable material.

15. The occlusion device of claim 13, wherein the spiral-shaped member of the first support member forms a first aperture within the first support member and the spiral-shaped member of the second support member forms a second aperture within the second support member and wherein the scaffold is configured to permit a medical device to pass through the first aperture and the second aperture.

16. The occlusion device of claim 13, wherein the fabric pouch includes an electrospun material.

17. The occlusion device of claim 13, wherein the first support member and the second support member are designed to press against tissue adjacent to the opening in the heart.

18. A method of occluding an opening in a heart, the method comprising:
   advancing an occlusion device to a position adjacent the opening, wherein the occlusion device includes:
      a framework including a first end region, a second end region and a medial region extending therebetween, wherein the first end region and second end region each includes a spiral-shaped member comprising a first wire portion and a second wire portion, wherein the first wire portion and the second wire portion spiral in parallel to one another and
      a biodegradable tissue ingrowth member extending over at least a portion of the framework;
         wherein the biodegradable tissue ingrowth member is configured to promote tissue ingrowth thereupon, and wherein the tissue ingrowth is configured to seal an opening in a heart;
   deploying the first end region on a first side of the opening;
   deploying the second end region on a second side of the opening opposite the first side.

19. The method of claim 18, wherein deploying the first end region on a first side of the opening includes positioning the framework against a tissue defining the first side of the opening.

20. The method of claim 19, wherein deploying the second end region on a second side of the opening includes positioning the framework against the tissue defining the second side of the opening such that the first end region and the second end region of the framework press against the tissue adjacent to the opening.

* * * * *